(12) United States Patent
Lucas et al.

(10) Patent No.: US 7,276,342 B2
(45) Date of Patent: Oct. 2, 2007

(54) XOBESIN AGONISTS AND ANTAGONISTS FOR THE TREATMENT OF METABOLIC DISORDERS

(75) Inventors: John Lucas, Concord, MA (US); Deno P. Dialynas, San Diego, CA (US); Kristen Briggs, Del Mar, CA (US)

(73) Assignee: Serono Genetics Institute S.A., Evry (FR)

( * ) Notice: Subject to any disclaimer, the term of this patent is extended or adjusted under 35 U.S.C. 154(b) by 310 days.

(21) Appl. No.: 10/485,233

(22) PCT Filed: Jul. 31, 2002

(86) PCT No.: PCT/IB02/03369

§ 371 (c)(1),
(2), (4) Date: Aug. 3, 2004

(87) PCT Pub. No.: WO03/011319

PCT Pub. Date: Feb. 13, 2003

(65) Prior Publication Data

US 2005/0003997 A1   Jan. 6, 2005

Related U.S. Application Data

(60) Provisional application No. 60/309,921, filed on Aug. 2, 2001.

(51) Int. Cl.
*G01N 33/53* (2006.01)
*C07K 14/00* (2006.01)
*A61K 38/00* (2006.01)

(52) U.S. Cl. .......................... 435/7.1; 530/350; 514/12

(58) Field of Classification Search ................ 530/350; 514/12; 435/69.1, 7.1; 536/23.1
See application file for complete search history.

(56) References Cited

U.S. PATENT DOCUMENTS

| 6,297,022 | B1 * | 10/2001 | McDonnell et al. ....... 435/7.21 |
| 6,344,441 | B1 * | 2/2002 | Bihain et al. ................ 514/12 |
| 6,461,821 | B1 | 10/2002 | Matsuzawa et al. |
| 6,566,332 | B2 | 5/2003 | Fruebis et al. |
| 6,579,852 | B2 | 6/2003 | Fruebis et al. |
| 6,867,189 | B2 | 3/2005 | Lucas et al. |
| 6,946,444 | B2 | 9/2005 | Bihain et al. |
| 6,967,091 | B2 | 11/2005 | Fruebis et al. |
| 6,989,367 | B2 | 1/2006 | Fruebis et al. |
| 2002/0151498 | A1 | 10/2002 | Bihain et al. |
| 2003/0215836 | A1 | 11/2003 | Young et al. |
| 2003/0224501 | A1 | 12/2003 | Young et al. |
| 2005/0054565 | A1 | 3/2005 | Lucas et al. |
| 2005/0069971 | A1 | 3/2005 | Lucas et al. |
| 2006/0089311 | A1 | 4/2006 | Dialynas et al. |

FOREIGN PATENT DOCUMENTS

| EP | 0911633 A1 | 4/1999 |
| EP | 1033134 A1 | 9/2000 |
| WO | WO99/46287 A1 | 9/1999 |
| WO | WO99/59618 A1 | 11/1999 |
| WO | WO 00/68380 A2 | 11/2000 |
| WO | WO 00/73448 A1 | 12/2000 |
| WO | WO 01/51645 A1 | 7/2001 |

OTHER PUBLICATIONS

STIC sequence alignment, OM protein-protein search using sw model, May 12, 2006, Issued patents -AA, pp. 1-2.*
U.S. Appl. No. 11/132,814, filed May 19, 2004, claims only.

* cited by examiner

*Primary Examiner*—Robert A. Wax
*Assistant Examiner*—Robert B Mondesi
(74) *Attorney, Agent, or Firm*—Saliwanchik, Lloyd & Saliwanchik

(57) ABSTRACT

The present invention relates to the field of metabolic research, in particular the discovery of compounds effective for reducing body mass and useful for treating obesity-related diseases and disorders. The obesity-related diseases or disorders envisioned to be treated by the methods of the invention include, but are not limited to, hyperlipidemia, atherosclerosis, insulin resistance, diabetes, and hypertension. In particular, the invention provides for methods of identifying and using AGONISTS and ANTAGONISTS of XOBESIN activity, wherein said activity is selected from the group consisting of lipid partitioning, lipid metabolism, and insulin-like activity.

4 Claims, No Drawings

XOBESIN AGONISTS AND ANTAGONISTS FOR THE TREATMENT OF METABOLIC DISORDERS

CROSS-REFERENCE TO RELATED APPLICATION

This application is the U.S. national stage application of International patent application No. PCT/IB02/03369, filed Jul. 31, 2002, which claims the benefit of U.S. Provisional Patent Application No. 60/309,921, filed Aug. 2, 2001.

FIELD OF THE INVENTION

The present invention relates to the field of metabolic research, in particular the discovery of compounds effective for reducing body mass and maintaining weight loss and useful for treating obesity-related diseases and disorders. The obesity-related diseases or disorders envisioned to be treated by the methods of the invention include, but are not limited to, hyperlipidemia, atherosclerosis, insulin resistance, diabetes, and hypertension. The present invention additionally relates elsewhere to the field of metabolic research, in particular the discovery of compounds effective for increasing body mass and useful for treating disorders associated with excessive weight loss. Applicant reserves the right to exclude any of the aforesaid obesity-related diseases or disorders. The disorders associated with excessive weight loss and envisioned to be treated by the methods of the invention include, but are not limited to, cachexia, cancer-related weight loss, AIDS-related weight loss, chronic inflammatory disease-related weight loss, and anorexia. Applicant reserves the right to exclude any of the aforesaid disorders associated with excessive weight loss.

In particular, the invention provides for methods of identifying and using AGONISTS and ANTAGONISTS of XOBESIN activity, wherein said activity is selected from the group consisting of lipid partitioning, lipid metabolism, and insulin-like activity.

BACKGROUND OF THE INVENTION

The following discussion is intended to facilitate the understanding of the invention, but is not intended nor admitted to be prior art to the invention.

Obesity is a public health problem that is serious, widespread, and increasing. In the United States, 20 percent of the population is obese; in Europe, a slightly lower percentage is obese (Friedman (2000) Nature 404:632-634). Obesity is associated with increased risk of hypertension, cardiovascular disease, diabetes, and cancer as well as respiratory complications and osteoarthritis (Kopelman (2000) Nature 404:635-643). Even modest weight loss ameliorates these associated conditions.

Recently it was shown that particular carboxyl-terminal fragments of the full-length ACRP30 (mouse) and APM1 (human) polypeptides have unexpected effects in vitro and in vivo, including utility for weight reduction, prevention of weight gain, and control of blood glucose levels (Fruebis et al (2001) Proc Natl Acad Sci USA 98:2005-10). The effects of ACRP30 fragment administration in mammals also include reduction of elevated free fatty acid levels including elevated free fatty acid levels caused by administration of epinephrine, iv. injection of "intralipid", or administration of a high fat test meal, as well as increased fatty acid oxidation in muscle cells, and weight reduction in mammals consuming a normal or high fat/high sucrose diet.

Throughout this application, various publications, patents and published patent applications are cited. The disclosures of these publications, patents and published patent specification referenced in this application are hereby incorporated by reference into the present disclosure to more fully describe the state of the art to which this invention pertains.

SUMMARY OF THE INVENTION

APM1 belongs to an expanding family of related secreted polypeptides that includes among others C2P, ZADJ-2 and ZADJ-7. These polypeptides have in common the structure: signal peptide, N-terminally disposed unique region, collagen-like region, and globular C-terminal C1q homology domain. APM1, C2P, ZADJ-2 and ZADJ-7 further share an NGLXXD amino acid motif C-terminally disposed within the globular domain within a loop implicated in receptor binding, wherein said receptor is XOBESIN. Fragments of APM1, C2P, ZADJ-2 and ZADJ-7 polypeptide comprising the globular domain are herein referred to as gAPM1, gC2P, gZADJ-2 and gZADJ-7. It is further taken to be understood herein that LIGAND refers to a composition consisting essentially of or consisting of in vitro or in vivo self-assembling homotrimer comprised of gAPM1, gC2P, gZADJ-2, or gZADJ-7 polypeptide fragment.

XOBESIN is a member of the Tumor Necrosis Factor Receptor Super Family (TNFRSF) and is a Type I transmembrane protein. The instant invention is based on XOBESIN as receptor for LIGAND that mediates effects, including utility for weight reduction, maintenance of weight loss, prevention of weight gain, increased insulin sensitivity, and control of blood glucose levels in humans and other mammals. These effects in mammals of XOBESIN engagement by LIGAND also include reduction of elevated free fatty acid levels including elevated free fatty acid levels including elevated free fatty acid levels caused by administration of epinephrine, i.v. injection of "intralipid", or administration of a high fat test meal, as well as increased fatty acid oxidation in muscle cells, and weight reduction in mammals consuming a normal or high fat/high sucrose diet. More specifically, the present invention is directed to XOBESIN to which LIGAND binds and through which LIGAND mediates said effects.

In particular, the invention provides for methods of identifying and using AGONISTS and ANTAGONISTS of XOBESIN activity, wherein said activity is selected from the group consisting of lipid partitioning, lipid metabolism, and insulin-like activity, as well as to pharmaceutical and physiologically acceptable compositions comprising said XOBESIN AGONISTS or ANTAGONISTS and methods of administering said pharmaceutical and physiologically acceptable compositions in order to increase or reduce body weight, maintain weight loss, or to treat obesity-related diseases and disorders. Assays for identifying AGONISTS and ANTAGONISTS of obesity-related activity are also part of the invention.

Preferably said XOBESIN AGONIST or ANTAGONIST is a compound selected from the group consisting of polypeptide, polypeptide fragment, peptide, protein, antibody, carbohydrate, lipid, small molecular weight organic compound and small molecular weight inorganic compound.

Preferably said XOBESIN AGONIST or ANTAGONIST is a compound that selectively binds to the extracellular domain of XOBESIN.

In other embodiment, said XOBESIN AGONIST or ANTAGONIST is a compound that selectively binds to the intracellular domain of a polypeptide comprising the extracellular domain of XOBESIN.

The present invention also provides a method of assaying test compounds to identify a test compound that binds to XOBESIN polypeptide. The method comprises contacting XOBESIN polypeptide with a test compound and to determine the extent of binding of the test compound to said XOBESIN polypeptide. The method further comprises determining whether such test compounds are AGONISTS or ANTAGONISTS of XOBESIN polypeptide. The present invention further provides a method of testing the impact of molecules on the expression of XOBESIN polypeptide or on the activity of XOBESIN polypeptide.

The present invention also relates to diagnostic methods of identifying individuals or non-human animals having elevated or reduced levels of XOBESIN products, which individuals are likely to benefit from therapies to suppress or enhance XOBESIN expression, respectively, and to methods of identifying individuals or non-human animals at increased risk for developing, or present state of having, certain diseases/disorders associated with XOBESIN abnormal expression or biological activity.

The present invention provides for methods of identifying AGONISTS of XOBESIN polypeptide biological activity comprising contacting a small molecule compound with XOBESIN polypeptides and measuring XOBESIN polypeptide biological activity in the presence and absence of these small molecules. The present invention further provides for methods of identifying ANTAGONISTS of XOBESIN polypeptide biological activity comprising contacting a small molecule compound with XOBESIN polypeptides and measuring XOBESIN polypeptide biological activity in the presence and absence of these small molecules. These small molecules can be a naturally occurring medicinal compound or derived from combinatorial chemical libraries.

The present invention also relates to pharmaceutical or physiologically acceptable compositions comprising, an active agent, including AGONIST or ANTAGONIST of the present invention.

In a first aspect, the invention is directed to XOBESIN AGONISTS, wherein said AGONIST is an antibody that specifically binds XOBESIN, a compound excluding said XOBESIN antibody (e.g., small organic or inorganic compound, protein, peptide, carbohydrate, lipid), or a LIGAND polypeptide or fragment thereof.

In a further preferred embodiment, the invention is directed to a XOBESIN AGONIST, wherein said AGONIST is an antibody that specifically binds XOBESIN. More preferably the invention is directed to said XOBESIN antibody, wherein said XOBESIN antibody binds XOBESIN and manifests LIGAND activity, wherein said activity is selected from the group consisting of lipid partitioning, lipid metabolism, and insulin-like activity or described herein.

In a further preferred embodiment, the invention is directed to a XOBESIN AGONIST, wherein said AGONIST is a compound excluding said XOBESIN antibody. More preferably the invention is directed to said compound, wherein said compound binds XOBESIN and manifests LIGAND activity, wherein said activity is selected from the group consisting of lipid partitioning, lipid metabolism, and insulin-like activity or described herein. Further more preferably the invention is directed to said compound, wherein said compound manifests LIGAND activity exclusive of binding to XOBESIN, wherein said activity is selected from the group consisting of lipid partitioning, lipid metabolism, and insulin-like activity or described herein. Further more preferably the invention is directed to said compound, wherein said compound increases XOBESIN expression.

In a further preferred embodiment, the invention is directed to a XOBESIN AGONIST that selectively binds to a polypeptide comprising the extracellular domain of XOBESIN.

In a further preferred embodiment, the invention is directed to a XOBESIN AGONIST, wherein said AGONIST is LIGAND, and wherein it is understood that LIGAND refers to a composition consisting essentially of or consisting of in vitro or in vivo self-assembling homotrimer comprised of gAPM1, gC2P, gZADJ-2, or gZADJ-7 polypeptide fragment. More preferably the invention is directed to said LIGAND, wherein said LIGAND binds XOBESIN and elicits biological activity, wherein said activity is selected from the group consisting of lipid partitioning, lipid metabolism, and insulin-like activity or described herein. More preferably the invention is directed to said LIGAND, wherein said LIGAND induces, enhances, or potentiates said biological activity exclusive of binding to XOBESIN. In preferred embodiment, said homotrimer is comprised of preferred gAPM1, gC2P, gZADJ-2 or gZADJ-7 polypeptide fragment APM1. Preferred gAPM1 polypeptide fragment is selected from amino acids 18-244, 34-244, 49-244, 56-244, 59-244, 66-244, 69-244, 78-244, 85-244, 93-244, 101-244, 102-244, 103-244, 104-244, 107-244, 110-244 or 113-244, wherein said numbering of said amino acids within APM1 amino acid sequence is understood to be taken from said APM1 amino acid sequence presented in Table 2. Less preferred gAPM1 fragments are indicated in bold.

C2P. Preferred gC2P polypeptide fragment is selected from amino acids 20-333, 25-333, 43-333, 45-333, 46-333, 50-333, 53-333, 61-333, 67-333, 74-333, 75-333, 77-333, 81-333, 82-333, 86-333, 89-333, 95-333, 100-333, 104-333, 113-333, 116-333, 125-333, 128-333, 140-333, 160-333, 164-333, 179-333, 182-333, 185-333, 188-333, 191-333, 193-333, or 202-333, wherein said numbering of said amino acids within C2P amino acid sequence is understood to be taken from said C2P amino acid sequence presented in Table 2. Less preferred gC2P fragments are indicated in bold.

ZADJ-2. Preferred gZADJ-2 polypeptide fragment is selected from amino acids 16-285, 25-285, 26285, 29-285, 30-285, 91-285, 93-285, 97-285, 98-285, 99-285, 105-285, 109-285, 112-285, 120-285, 126-285, 127-285, 130-285, 132-285, 133-285, 134-285, or 150-285, wherein said numbering of said amino acids within ZADJ-2 amino acid sequence is understood to be taken from said ZADJ-2 amino acid sequence presented in Table 2. Less preferred gZADJ-2 fragments are indicated in bold.

ZADJ-7. Preferred gZADJ-7 polypeptide fragment is selected from amino acids 31-303, 39-303, 78-303, 81-303, 84-303, 85-303, 88-303, 91-303, 97-303, 99-303, 109-303, 117-303, 118-303, 127-303, 139-303, 142-303, 155-303, or 162-303, wherein said numbering of said amino acids within ZADJ-7 amino acid sequence is understood to be taken from said ZADJ-7 amino acid sequence presented in Table 2. Less preferred gZADJ-7 fragments are indicated in bold.

More preferred LIGAND is APM1.

In a further preferred embodiment, said AGONIST is able to lower circulating (either blood, serum or plasma) levels (concentration) of: (i) free fatty acids, (ii) glucose, and/or (iii) triglycerides.

Further preferred AGONISTS are those that significantly stimulate muscle lipid or free fatty acid oxidation as compared to untreated cells. Further preferred AGONISTS are those that cause C2C12 cells differentiated in the presence of said AGONISTS to undergo at least 10%, 20%, 30%, 35%, or 40% more oleate oxidation as compared to untreated cells.

Further preferred AGONISTS are those that increase by at least 10%, 20%, 30%, 35%, or 40% leptin uptake in a liver cell line [preferably BPRCL mouse liver cells (ATCC CRL-2217)] as compared to untreated cells.

Further preferred AGONISTS are those that significantly reduce the postprandial increase in plasma free fatty acids or triglycerides, particularly following a high fat meal.

Further preferred AGONISTS are those that significantly reduce or eliminate ketone body production, particularly following a high fat meal.

Further preferred AGONISTS are those that increase glucose uptake in skeletal muscle cells.

Further preferred AGONISTS are those that increase glucose uptake in adipose cells.

Further preferred AGONISTS are those that increase glucose uptake in neuronal cells.

Further preferred AGONISTS are those that increase glucose uptake in red blood cells.

Further preferred AGONISTS are those that increase glucose uptake in the brain.

Further preferred AGONISTS are those that significantly reduce the postprandial increase in plasma glucose following a meal, particularly a high carbohydrate meal.

Further preferred AGONISTS are those that significantly prevent the postprandial increase in plasma glucose following a meal, particularly a high fat or a high carbohydrate meal.

Further preferred AGONISTS are those that improve insulin sensitivity.

Further preferred said AGONISTS are those that decrease body mass, wherein said decrease in body mass is comprised of a change in mass of the subcutaneous adipose tissue.

Further preferred said AGONISTS are those that decrease body mass, wherein said decrease in body mass is comprised of a change in mass of the visceral (omental) adipose tissue.

In a second aspect, the invention features a pharmaceutical or physiologically acceptable composition comprising, consisting essentially of, or consisting of, said AGONIST described in the first aspect and, alternatively, a pharmaceutical or physiologically acceptable diluent.

In a third aspect, the invention features a method of reducing body mass comprising providing or administering to individuals in need of reducing body mass said pharmaceutical or physiologically acceptable composition described in the second aspect.

In a fourth aspect, the invention features a method of preventing or treating an obesity-related disease or disorder comprising providing or administering to an individual in need of such treatment said pharmaceutical or physiologically acceptable composition described in the second aspect. Preferably, said obesity-related disease or disorder is selected from the group consisting of obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by said XOBESIN AGONIST of the invention include hyperlipidemia and hyperuricemia. In preferred embodiments, said individual is a mammal, preferably a human.

In related aspects, embodiments of the present invention includes methods of causing or inducing a desired biological response in an individual comprising the steps of: providing or administering to an individual a composition comprising AGONIST, wherein said biological response is selected from the group consisting of:

(a) lowering circulating (either blood, serum, or plasma) levels (concentration) of free fatty acids;

(b) lowering circulating (either blood, serum or plasma) levels (concentration) of glucose;

(c) lowering circulating (either blood, serum or plasma) levels (concentration) of triglycerides;

(d) stimulating muscle lipid or free fatty acid oxidation;

(e) increasing leptin uptake in the liver or liver cells;

(e) reducing the postprandial increase in plasma free fatty acids, particularly following a high fat meal;

(f) reducing or eliminating ketone body production, particularly following a high fat meal;

(g) increasing tissue sensitivity to insulin, particularly muscle, adipose, liver or brain, and further wherein said biological response is significantly greater than, or at least 10%, 20%, 30%, 35%, or 40% greater than that observed in the absence of treatment; or alternatively wherein said biological response is greater than a transient response; or alternatively wherein said biological response is sustained. In further preferred embodiments, the present invention of said pharmaceutical or physiologically acceptable composition can be used as a method to control blood glucose in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control body weight in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control blood glucose in some persons with Noninsulin Dependent Diabetes Mellitus (NIDDM, Type II diabetes) alone, without combination of insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) alone, without combination of insulin therapy.

In further preferred embodiments, the present invention of said pharmaceutical or physiologically acceptable composition can be used as a method to control body weight in some persons with Noninsulin Dependent Diabetes Mellitus (NIDDM, Type II diabetes) alone, without combination of insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) alone, without combination of insulin therapy.

In a further preferred embodiment, the present invention may be used in complementary therapy of NIDDM patients to improve their weight or glucose control in combination with an insulin secretagogue or an insulin sensitising agent. Preferably, the insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of NIDDM patients alone, without an insulin secretagogue or an insulin sensitising agent.

In a further preferred embodiment, the present invention may be used in complementary therapy of IDDM patients to improve their weight or glucose control in combination with an insulin secretagogue or an insulin sensitising agent. Preferably, the insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of IDDM patients alone, without an insulin secretagogue or an insulin sensitising agent.

In a further preferred embodiment, the present invention may be administered either concomitantly or concurrently, with the insulin secretagogue or insulin sensitising agent for example in the form of separate dosage units to be used simultaneously, separately or sequentially (either before or after the secretagogue or either before or after the sensitising agent). Accordingly, the present invention further provides for a composition of pharmaceutical or physiologically acceptable composition and an insulin secretagogue or insulin sensitising agent as a combined preparation for simultaneous, separate or sequential use for the improvement of body weight or glucose control in NIDDM or IDDM patients.

In further preferred embodiments, the present invention of said pharmaceutical or physiologically acceptable composition further provides a method for the use as an insulin sensitiser.

In further preferred embodiments, the present invention of said pharmaceutical or physiologically acceptable composition can be used as a method to improve insulin sensitivity in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to improve insulin sensitivity in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to improve insulin sensitivity in some persons with Noninsulin Dependent Diabetes Mellitus (NIDDM, Type II diabetes) without insulin therapy.

In a fifth aspect, the invention features a use of AGONIST described in the first aspect for treatment of obesity-related diseases and disorders and/or reducing body mass. Preferably, said obesity-related diseases and disorders are selected from the group consisting of obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by said AGONIST of the invention include hyperlipidemia and hyperuricemia.

In a sixth aspect, the invention features a use of AGONIST described in the first aspect for the preparation of a medicament for the treatment of obesity-related diseases and disorders and/or for reducing body mass. Preferably, said obesity-related disease or disorder is selected from the group consisting of obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. In referred embodiments, said individual is a mammal, preferably a human.

In a seventh aspect, the invention provides AGONIST of the first aspect of the invention, or a composition of the second aspect of the invention, for use in a method of treatment of the human or animal body.

In an eighth aspect, the invention features methods of reducing body weight comprising providing to an individual said pharmaceutical or physiologically acceptable composition described in the second aspect, or AGONIST described in the first aspect. Where the reduction of body weight is practiced for cosmetic purposes, the individual has a BMI of at least 20 and no more than 25. In embodiments for the treatment of obesity, the individual may have a BMI of at least 20. One embodiment for the treatment of obesity provides for the treatment of individuals with BMI values of at least 25. Another embodiment for the treatment of obesity provides for the treatment of individuals with BMI values of at least 30. Yet another embodiment provides for the treatment of individuals with BMI values of at least 40.

In further embodiment, the invention features methods of maintaining weight loss comprising providing to an individual said pharmaceutical or physiologically acceptable composition.

In a ninth aspect, the invention features the pharmaceutical or physiologically acceptable composition described in the second aspect for reducing body mass and/or for treatment or prevention of obesity-related diseases or disorders.

Preferably, said obesity-related disease or disorder is selected from the group consisting of obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. In preferred embodiments, said individual is a mammal, preferably a human. In preferred embodiments, the identification of said individuals to be treated with said pharmaceutical or physiologically acceptable composition comprises genotyping LIGAND single nucleotide polymorphisms (SNPs) or measuring LIGAND polypeptide or mRNA levels in clinical samples from said individuals. Preferably, said clinical samples are selected from the group consisting of blood, serum, plasma, urine, and saliva.

In a tenth aspect, the invention features the pharmaceutical or physiologically acceptable composition described in the second aspect for reducing body weight for cosmetic reasons.

In an eleventh aspect, AGONIST of the invention is used in methods of treating insulin resistance comprising providing to an individual said pharmaceutical or physiologically acceptable composition described in the second aspect, or AGONIST described in the first aspect.

In a preferred aspect of the methods above and disclosed herein, the amount of AGONIST administered to an individual is sufficient to bring levels of XOBESIN activation to their normal levels (levels in individuals without obesity-related disease or disorder). "Normal levels" of XOBESIN activation may be followed using surrogate markers including circulating (either blood, serum or plasma) levels (concentration) of: (i) free fatty acids, (ii) glucose, and/or (iii) triglycerides.

In a twelfth aspect, the invention is directed to a XOBESIN ANTAGONIST, wherein said ANTAGONIST is a soluble fragment of XOBESIN polypeptide, an antibody that specifically binds XOBESIN, a compound excluding said soluble fragment of XOBESIN polypeptide and said XOBESIN antibody (e.g., small molecular weight organic or inorganic compound, protein, peptide, carbohydrate, lipid), or a variant or fragment of LIGAND polypeptide.

In a further preferred embodiment, the invention is directed to a XOBESIN ANTAGONIST, wherein said ANTAGONIST is a soluble fragment of XOBESIN polypeptide. More preferably the invention is directed to purified, isolated, or recombinant soluble fragments of XOBESIN polypeptide. More preferably the invention is directed to said soluble fragment of XOBESIN polypeptide, wherein said soluble fragment binds LIGAND and blocks LIGAND activity, said activity being selected from the group consisting of lipid partitioning, lipid metabolism, and insulin-like activity or described herein, and wherein said soluble fragment of XOBESIN polypeptide does not activate XOBESIN. Preferably said soluble fragment of XOBESIN polypeptide blocks or inhibits LIGAND binding to XOBESIN. In preferred embodiments, said soluble fragment of XOBESIN polypeptide comprises, consists essentially of, or consists of, at least 6 and not more than 246 consecutive amino acids of SEQ ID NO:2, more preferably of amino acids comprising the extracellular domain of XOBESIN. Preferred said soluble fragment of XOBESIN comprises the extracellular domain of mature XOBESIN polypeptide. Particularly preferred soluble fragment of XOBESIN comprises amino acids 30-197, 30-199, 30-207, 30-212, 30-224, 30-231, 30-245 or 30-262 of SEQ ID NO:2, where it is understood that amino acid 30 is predicted to be the N-terminal amino acid of the mature XOBESIN polypeptide absent the putative signal peptide. In other preferred embodiments, said soluble fragment of XOBESIN polypeptide comprises an amino acid sequence at least 80%, 85%, 90%, 91%, 92%, 93%, 94%, 95%, 96%, 97%, 98%, or 99% identical to the corresponding consecutive amino acids of SEQ ID NO:2. Further preferred embodiments include heterologous polypeptides comprising a XOBESIN polypeptide of the invention. In further preferred embodiment, a XOBESIN polypeptide of the invention is conjugated at its N- or C-terminus to an antibody Fc region or portion thereof.

In a further preferred embodiment, the invention is directed to a XOBESIN ANTAGONIST, wherein said ANTAGONIST is an antibody that specifically binds XOBESIN. More preferably the invention is directed to said XOBESIN antibody, wherein said XOBESIN antibody binds XOBESIN and blocks LIGAND activity, said activity being selected from the group consisting of lipid partitioning, lipid metabolism, and insulin-like activity or described herein, and wherein said XOBESIN antibody does not activate XOBESIN. Preferably said XOBESIN antibody blocks or inhibits LIGAND binding to XOBESIN.

In a further preferred embodiment, the invention is directed to a XOBESIN ANTAGONIST, wherein said ANTAGONIST is a compound excluding said soluble fragment of XOBESIN polypeptide and said XOBESIN antibody (e.g., small organic molecule, protein, peptide). More preferably the invention is directed to said compound, wherein said compound binds to XOBESIN and blocks LIGAND activity, said activity being selected from the group consisting of lipid partitioning, lipid metabolism, and insulin-like activity or described herein, and wherein said compound does not activate XOBESIN. Preferably said compound that binds to XOBESIN blocks or inhibits LIGAND binding to XOBESIN. Further more preferably the invention is directed to said compound, wherein said compound blocks or inhibits LIGAND activity exclusive of binding to XOBESIN, said activity being selected from the group consisting of lipid partitioning, lipid metabolism, and insulin-like activity or described herein, and wherein said compound does not activate XOBESIN. Further more preferably the invention is directed to said compound, wherein said compound blocks or inhibits XOBESIN expression and wherein said compound does not have LIGAND activity, said activity being selected from the group consisting of lipid partitioning, lipid metabolism, and insulin-like activity or described herein, and wherein said compound does not activate XOBESIN.

In a further preferred embodiment, the invention is directed to a XOBESIN ANTAGONIST, wherein said ANTAGONIST is a variant or fragment of LIGAND polypeptide. More preferably the invention is directed to said variant of fragment of LIGAND polypeptide, wherein said variant or fragment of LIGAND polypeptide binds XOBESIN and blocks LIGAND activity, said activity being selected from the group consisting of lipid partitioning, lipid metabolism, and insulin-like activity or described herein, and wherein said variant or fragment of LIGAND polypeptide does not activate XOBESIN. Preferably said variant or fragment of LIGAND polypeptide blocks or inhibits LIGAND binding to XOBESIN. More preferably the invention is directed to said variant or fragment of LIGAND polypeptide, wherein said variant or fragment of LIGAND polypeptide inhibits the induction, enhancement, or potentiation of said biological activity exclusive of binding to XOBESIN.

In a further preferred embodiment, the invention is directed to a XOBESIN ANTAGONIST that selectively binds to a polypeptide comprising the extracellular domain of XOBESIN.

In a further preferred embodiment, said ANTAGONIST is able to raise circulating (either blood, serum or plasma) levels (concentration) of: (i) free fatty acids, (ii) glucose, and/or (iii) triglycerides.

Further preferred said ANTAGONISTS are those that significantly inhibit muscle lipid or free fatty acid oxidation stimulated by its LIGAND. Further preferred said ANTAGONISTS are those that cause C2C12 cells differentiated in the presence of LIGAND to undergo at least 10%, 20%, 30%, 35%, or 40% less oleate oxidation as compared to untreated cells.

Further preferred said ANTAGONISTS are those that inhibit by at least 10%, 20%, 30%, 35%, or 40% the increase in leptin uptake stimulated by LIGAND polypeptide in a liver cell line [preferably BPRCL mouse liver cells (ATCC CRL-2217)] as compared to untreated cells.

Further preferred said ANTAGONISTS are those that significantly increase the postprandial increase in plasma free fatty acids, particularly following a high fat meal.

Further preferred said ANTAGONISTS are those that significantly increase ketone body production, particularly following a high fat meal.

Further preferred said ANTAGONISTS are those that decrease glucose uptake in skeletal muscle cells stimulated by LIGAND.

Further preferred said ANTAGONISTS are those that decrease glucose uptake in adipose cells stimulated by LIGAND.

Further preferred said ANTAGONISTS are those that decrease glucose uptake in neuronal cells stimulated by LIGAND.

Further preferred said ANTAGONISTS are those that decrease glucose uptake in red blood cells stimulated by LIGAND.

Further preferred said ANTAGONISTS are those that decrease glucose uptake in the brain stimulated by LIGAND.

Further preferred said ANTAGONISTS are those that significantly increase the postprandial increase in plasma glucose following a meal, particularly a high carbohydrate meal.

Further preferred said ANTAGONISTS are those that significantly facilitate the postprandial increase in plasma glucose following a meal, particularly a high fat or a high carbohydrate meal.

Further preferred said ANTAGONISTS are those that reduce the insulin sensitivity stimulated by LIGAND.

Further preferred said ANTAGONISTS are those that increase body mass, wherein said increase in body mass is comprised of a change in mass of the subcutaneous adipose tissue.

Further preferred said ANTAGONISTS are those that increase body mass, wherein said increase in body mass is comprised of a change in mass of the visceral (omental) adipose tissue.

In a thirteenth aspect, the invention features a pharmaceutical or physiologically acceptable composition comprising, consisting essentially of, or consisting of, said ANTAGONIST described in the twelfth aspect and, alternatively, a pharmaceutical or physiologically acceptable diluent.

In a fourteenth aspect, the invention features a method of increasing body mass comprising providing or administering to individuals in need of increasing body mass said pharmaceutical or physiologically acceptable composition described in the thirteenth aspect.

In a fifteenth aspect, the invention features a method of preventing or treating disorders associated with excessive weight loss comprising providing or administering to an individual in need of such treatment said pharmaceutical or physiologically acceptable composition described in the thirteenth aspect. Preferably said disorder is selected from the group consisting of cachexia, wasting, cancer-related weight loss, AIDS-related weight loss, chronic inflammatory disease-related weight loss, anorexia, and bulimia. Said disorders associated with excessive weight loss are comprised of those mediated by tumor necrosis factor (TNFalpha) alone, those mediated by TNFalpha plus one or more additional factors, and those mediated only by one or more factors exclusive of TNFalpha. Said factors include, but are not restricted to, macrophage migration inhibitory factor, interleukin 1, and interleukin 6. In preferred embodiments, said individual is a mammal, preferably a human.

In related aspects, embodiments of the present invention includes methods of causing or inducing a desired biological response in an individual comprising the steps of: providing or administering to an individual a composition comprising ANTAGONIST, wherein said biological response is selected from the group consisting of:
  (a) raising circulating (either blood, serum, or plasma) levels (concentration) of free fatty acids (FFA) or triglycerides (TG);
  (b) raising circulating (either blood, serum or plasma) levels (concentration) of glucose;
  (c) raising circulating (either blood, serum or plasma) levels (concentration) of triglycerides;
  (d) inhibiting muscle lipid or free fatty acid oxidation;
  (e) inhibiting leptin uptake in the liver or liver cells;
  (e) increasing the postprandial increase in plasma free fatty acids, particularly following a high fat meal; and,
  (f) increasing or eliminating ketone body production, particularly following a high fit meal;
  (g) reducing tissue sensitivity to insulin, particularly muscle, adipose, liver or brain, and further wherein said biological response is greater than a transient response; or alternatively herein said biological response is sustained. In further preferred embodiments, the present invention of said pharmaceutical or physiologically acceptable composition can be used as a method of increasing body mass in some persons with cachexia, wasting, cancer-related weight loss, AIDS-related weight loss, chronic inflammatory disease-related weight loss, anorexia, and bulimia.

In further preferred embodiments, the present invention of said pharmaceutical or physiologically acceptable composition further provides a method for the use as an insulin de-sensitiser, wherein the sensitivity of a cell or tissue to insulin is reduced.

In a sixteenth aspect, the invention features a method of making the XOBESIN polypeptide described in the twelfth aspect, wherein said method is selected from the group consisting of proteolytic cleavage, recombinant methodology and artificial synthesis. In a preferred embodiment, proteolytic cleavage is carried out using tr In a seventeenth aspect, the invention features a use of ANTAGONIST described in the twelfth aspect for the preparation of a medicament for the treatment of disorders associated with excessive weight loss and/or for increasing body mass. Preferably, said disorder is selected from the group consisting of cachexia, wasting, cancer-related weight loss, AIDS-related weight loss, chronic inflammatory disease-related weight loss, anorexia, and bulimia. In preferred embodiments, said individual is a mammal, preferably a human.

In an eighteenth aspect, the invention provides ANTAGONIST of the twelfth aspect of the invention, or a composition of the thirteenth aspect of the invention, for use in a method of treatment of the human or animal body.

In a nineteenth aspect, the invention features methods of increasing body weight comprising providing to an individual said pharmaceutical or physiologically acceptable composition described in the thirteenth aspect, or ANTAGONIST described in the twelfth aspect. Where the increase of body weight is practiced for cosmetic purposes, the individual has a BMI of no greater than 25 and at least 20. In embodiments for the treatment of disorders associated with excessive weight loss, the individual may have a BMI no greater than 20. One embodiment for the treatment of disorders associated with excessive weight loss provides for the treatment of individuals with BMI values of no greater than 15. Alternatively, for increasing the body weight of an individual, the BMI value should be at least 15 and no more than 20.

In a twentieth aspect, the invention features the pharmaceutical or physiologically acceptable composition described in the thirteenth aspect for increasing body mass and/or for treatment of disorders associated with excessive weight loss. Preferably, said disorder is selected from the group consisting of cachexia, wasting, cancer-related weight loss, AIDS-related weight loss, chronic inflammatory disease-related weight loss, anorexia, and bulimia. In preferred embodiments, said individual is a mammal, preferably a human.

In a twenty-first aspect, the invention features the pharmaceutical or physiologically acceptable composition described in the thirteenth aspect for increasing body weight for cosmetic reasons.

In a preferred aspect of the methods above and disclosed herein, the amount of ANTAGONIST administered to an individual is sufficient to bring levels of XOBESIN activation to their normal levels (levels in healthy individuals). "Normal levels" of XOBESIN activation may be followed using surrogate markers including circulating (either blood, serum or plasma) levels (concentration) of: (i) free fatty acids, (ii) glucose, and/or (iii) triglycerides.

BRIEF DESCRIPTION OF TABLES

Table 1 lists known or predicted biologic structural and functional domains for the XOBESIN polypeptide of SEQ ID NO:2 of the present invention, including the signal peptide, extracellular (EC) domain, transmembrane domain, and intracellular (IC) domain.

Table 2 lists the amino acid sequence of full-length APM1 (SEQ ID NO: 3), C2P (SEQ ID NO: 4), ZADJ-2 (SEQ ID NO: 5) and ZADJ-7 (SEQ ID NO: 6) polypeptide. The total number of amino acids is given in parentheses. The predicted signal peptide is indicated in bold. The collagen-like region is indicated by dotted line. The region between the predicted signal peptide and the collagen-like region is the N-terminally disposed unique region. The globular C-terminal Cl q homology domain is indicated by single underline. The NGLXXD amino acid motif C-terminally disposed within the globular domain is indicated by double underline. It is taken to be understood that C2P herein encompasses variants comprising the substitution of valine for methionine at position 219 and/or the substitution of methionine for valine at position 301.

STRUCTURE OF XOBESIN POLYPEPTIDE

The full-length XOBESIN polypeptide is comprised of at least 4 distinct regions including:
1. an N-terminal putative signal peptide comprising amino acids from about amino acids 1-29 of SEQ ID NO:2;
2. an extracellular domain comprising a LIGAND binding portion and comprising amino acids from about amino acids 30-275 of SEQ ID NO:2;
3. a transmembrane domain comprising amino acids from about amino acids 276-298 of SEQ D NO:2; and
4. an intracellular domain of the polypeptide is amino acid 299 of SEQ ID NO:2.

BRIEF DESCRIPTION OF SEQUENCE LISTING

SEQ ID NO:1 is the nucleotide sequence of cDNA with an open reading frame which location is indicated as features. When appropriate, the locations of the potential polyadenylation site and polyadenylation signal are also indicated.

SEQ ID NO:2 is the amino acid sequence of polypeptide encoded by the cDNA of SEQ ID NO:1.

SEQ ID NO: 3 is the amino acid sequence of the full-length APM1 polypeptide.

SEQ ID NO: 4 is the amino acid sequence of the full-length C2P polypeptide.

SEQ ID NO: 5 is the amino acid sequence of the full-length ZADJ-2 polypeptide.

SEQ ID NO: 6 is the amino acid sequence of the full-length ZADJ-7 polypeptide.

The appended Sequence Listing is hereby incorporated by reference in its entirety.

DETAILED DESCRIPTION

Definitions

Before describing the invention in greater detail, the following definitions are set forth to illustrate and define the meaning and scope of the terms used to describe the invention herein.

The term "isolated" requires that the material be removed from its original environment (e.g., the natural environment if the material is naturally occurring).

The term "purified" does not require absolute purity; rather, it is intended as a relative definition. Purification of starting material or natural material to at least one order of magnitude, preferably two or three orders, and more preferably four or five orders of magnitude is expressly contemplated.

As used interchangeably herein, the term "polynucleotide(s)" include RNA or DNA (either single or double stranded, coding, complementary or antisense), or RNA/DNA hybrid sequences of more than one nucleotide in either single chain or duplex form (although each of the above species may be particularly specified).

The terms "complementary" or "complement thereof" are used herein to refer to the sequences of polynucleotides that are capable of forming Watson & Crick base pairing with another specified polynucleotide throughout the entirety of the complementary region.

The terms "polypeptide" and "protein", used interchangeably herein, refer to a polymer of amino acids without regard to the length of the polymer; thus, peptides, oligopeptides, and proteins are included within the definition of polypeptide. This term also does not specify or exclude chemical or post-expression modifications of the polypeptides of the invention, although chemical or post-expression modifications of these polypeptides may be included excluded as specific embodiments.

As used herein, the terms "recombinant polynucleotide" and "polynucleotide construct" are used interchangeably to refer to linear or circular, purified or isolated polynucleotides that have been artificially designed and which comprise at least two nucleotide sequences that are not found as contiguous nucleotide sequences in their initial natural environment. In particular, these terms mean that the polynucleotide or cDNA is adjacent to "backbone" nucleic acid to which it is not adjacent in its natural environment.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

As used herein, the term "operably linked" refers to a linkage of polynucleotide elements in a functional relationship.

As used herein, the term "non-human animal" refers to any non-human animal, including insects, birds, rodents and more usually mammals. Both the terms "animal" and "mammal" expressly embrace human subjects unless preceded with the term "non-human".

The term "domain" refers to an amino acid fragment with specific biological properties. This term encompasses all known structural and linear biological motifs.

As used herein, the term "receptor" refers to a polypeptide to which a "ligand" binds and through which said "ligand" elicits a biological response comprised of biological activities. Said receptor is preferably XOBESIN of the present invention. Said "ligand" is preferably LIGAND of the present invention. By "receptor activation" is intended "ligand"-mediated alteration of said receptor polypeptide, wherein said alteration is selected from but not limited to the group consisting of receptor alterations associated with said biological response.

As used herein, the term "AGONIST" refers to naturally occurring and synthetic compounds capable of inducing, enhancing, or potentiating a biological response comprised of biological activities.

As used herein, the term "ANTAGONIST" refers to naturally occurring and synthetic compounds capable of inhibiting a biological response, inhibiting the induction of a biological response, or inhibiting the potentiation of a biological response, wherein said biological response is comprised of biological activities.

Without being limited by theory, the compounds/polypeptides of the invention are capable of modulating the partitioning of dietary lipids between the liver and peripheral tissues, and are thus believed to treat "diseases involving the partitioning of dietary lipids between the liver and peripheral tissues." The term "peripheral tissues" is meant to include muscle and adipose tissue. In preferred embodiments, the compounds/polypeptides of the invention partition the dietary lipids toward or away from the muscle. In alternative preferred embodiments, the dietary lipids are partitioned toward or away from the adipose tissue. In other preferred embodiments, the dietary lipids are partitioned toward or away from the liver. In yet other preferred embodiments, the compounds/polypeptides of the invention increase or decrease the oxidation of dietary lipids, preferably free fatty acids (FFA) by the muscle. Dietary lipids include, but are not limited to triglycerides and free fatty acids.

Preferred diseases believed to involve the partitioning of dietary lipids include obesity-related diseases and disorders such as obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other disorders of the invention include disorders associated with excessive weight loss such as cachexia, wasting, cancer-related weight loss, AIDS-related weight loss, chronic inflammatory disease-related weight loss, anorexia, and bulimia.

The terms "comprising", "consisting of" and "consisting essentially of" may be interchanged for one another throughout the instant application, although each retains its normal definition. The term "having" has the same meaning as "comprising" and may be replaced with either the term "consisting of" or "consisting essentially of".

Polypeptides of the Invention

Preferably, polypeptides of the invention are recombinantly produced using routine expression methods known in the art. The polynucleotide encoding the desired polypeptide is operably linked to a promoter into an expression vector suitable for any convenient host Both eukaryotic and prokaryotic host systems are used in forming recombinant polypeptides. The polypeptide is then isolated from lysed cells or from the culture medium and purified to the extent needed for its intended use.

Consequently, a further embodiment of the present invention is a method of making a polypeptide, said method comprising the steps of
  a) obtaining a cDNA encoding said polypeptide;
  b) inserting said cDNA in an expression vector such that the cDNA is operably linked to a promoter; and
  c) introducing said expression vector into a host cell whereby said host cell produces said polypeptide.

In one aspect of this embodiment, the method further comprises the step of isolating the polypeptide. Another embodiment of the present invention is a polypeptide obtainable by the method described in the preceding paragraph.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). In preferred embodiment, recombinant polypeptides of the invention are expressed in mammalian cells.

The invention is drawn, inter alia, to isolated, purified or recombinant polypeptides. XOBESIN polypeptides of the invention are useful for increasing (ANTAGONISTS of XOBESIN) body weight either as a cosmetic treatment or for treatment or prevention of diseases and disorders as discussed or described herein. XOBESIN polypeptides are also useful inter alia in screening assays for AGONISTS or ANTAGONISTS of XOBESIN activity and for raising XOBESIN-specific antibodies. When used for cosmetic treatments, or for the treatment or prevention of diseases, disorders, or conditions, one or more XOBESIN polypeptides can be provided to a subject. Thus, various fragments of the full-length protein can be combined into a "cocktail" for use in the various treatment regimens. LIGAND polypeptides of the invention are useful for reducing (AGONISTS of XOBESIN) body weight either as a cosmetic treatment or prevention of diseases and disorders as discussed or described herein.

The XOBESIN polypeptides of the present invention are preferably provided in an isolated form, and may be partially or substantially purified.

Modifying XOBESIN Biological Activity

Modifying endogenous XOBESIN biological activity is expressly contemplated by the present invention. The present invention further relates to compounds able to modulate XOBESIN biological activity and methods to use these compounds. Such compounds may interact with XOBESIN polypeptides directly or indirectly.

Candidate AGONISTS and ANTAGONISTS Obtained by Optical Biosensor Methods

Compounds interacting with a polypeptide comprising XOBESIN extracellular domain can be screened by using an Optical Biosensor as described in Edwards and Leatherbarrow (1997) and also in Szabo et al. (1995), the disclosures of which are incorporated by reference. This technique permits the detection of interactions between molecules in real time, without the need of labeled molecules. This technique, which is based on the surface plasmon resonance (SPR) phenomenon, is presented in more detail in Example 1.

Compounds Modulating XOBESIN Biological Activity

Another method of screening for compounds that modulate XOBESIN biological activity is by measuring the effects of test compounds on specific biological activity, wherein said activity is selected from the group consisting of lipid partitioning, lipid metabolism, and insulin-like activity or as described herein, in a host cell. In one embodiment, the present invention relates to a method of identifying an agent that alters XOBESIN activity, wherein a nucleic acid construct comprising the polynucleotide of SEQ ID NO:1 or a fragment thereof encoding full length XOBESIN polypeptide is introduced into a mammalian host cell. The transfected mammalian host cells are maintained under conditions appropriate for expression of the encoded XOBESIN, whereby the nucleic acid is expressed. The host cells are then contacted with a compound to be assessed (an agent) and an activity of the cells is detected in the presence of the compound to be assessed, wherein said activity is selected from the group consisting of lipid partitioning, lipid metabolism, and insulin-like activity or as described herein. Detection of a change in said activity for said transfected host cell, but not in untransfected host cell, in the presence of the agent indicates that the agent alters XOBESIN activity. In a particular embodiment, the invention relates to a method of identifying an agent which is an activator (AGONIST) of XOBESIN activity, wherein detection of an increase of said activity, said activity being selected from the group consisting of lipid partitioning, lipid metabolism, and insulin-like activity or as described herein, in the presence of the agent indicates that the agent activates XOBESIN activity. In another particular embodiment, the invention relates to a method of identifying an agent which is an inhibitor (ANTAGONIST) of XOBESIN activity, wherein detection of a decrease of said activity, said activity being selected from the group consisting of lipid partitioning, lipid metabolism, and insulin-like activity or as described herein, in the presence of the agent indicates that the agent inhibits XOBESIN activity.

Detection of a change in said XOBESIN activity, said activity being selected from the group consisting of lipid partitioning, lipid metabolism, and insulin-like activity or as described herein, can be performed using a variety of techniques as described for representative activities in Examples provided herein.

In a particular embodiment a high throughput screen can be used to identify agents that activate (enhance) or inhibit XOBESIN activity (See e.g., PCT publication WO 98/45438, which disclosure is hereby incorporated by reference in its entirety).

Methods of Screening for Compounds Modulating XOBESIN Activity

The present invention also relates to methods of screening compounds for their ability to modulate (e.g. increase or inhibit) the activity or expression of XOBESIN. More specifically, the present invention relates to methods of testing compounds for their ability either to increase or to decrease activity of XOBESIN. The assays are performed in vitro or in vivo.

The present invention relates to a method for the screening of a candidate substance for interaction with a polypeptide comprising XOBESIN extracellular domain, said method comprising the following steps:
  a) providing said polypeptide comprising XOBESIN extracellular domain;
  b) obtaining a candidate substance;
  c) bringing into contact said polypeptide with said candidate substance;
  d) detecting the complexes formed between said polypeptide and said candidate substance.

The invention further relates to a method for the production of a pharmaceutical composition comprising a method for the screening of a candidate substance that interact with a XOBESIN polypeptide, fragments or variants thereof and furthermore mixing the identified substance with a pharmaceutically acceptable carrier.

The present invention relates to a method for the screening of a candidate substance for the capacity to increase expression of XOBESIN, said method comprising the following steps:
  a) isolating mRNA from cells which have or have not been contacted with said candidate substance;
  b) carrying out a Northern blot analysis with labeled cDNA probe encoding all or part of XOBESIN polypeptide;
  c) wherein increased signal in cells having been contacted with said candidate substance over that of uncontacted cells is taken to indicate that said candidate substance increases expression of XOBESIN and is an AGONIST of XOBESIN activity; and d) wherein decreased signal in cells having been contacted with said candidate substance over that of uncontacted cells is taken to indicate that said candidate substance decreases expression of XOBESIN and is an ANTAGONIST of XOBESIN activity.

Methods of isolating mRNA and carrying out Northern blot analysis are well known to those of ordinary skill in the art.

Preparation of Antibody Compositions

Substantially pure protein or polypeptide is isolated from transfected or transformed cells containing an expression vector encoding the XOBESIN protein or a portion thereof. The concentration of protein in the final preparation is adjusted, for example, by concentration on an Amicon filter device, to the level of a few micrograms/ml. Monoclonal or polyclonal antibody to the protein can then be prepared by methods well known to those of ordinary skill in the art Preferably the present invention includes monoclonal and polyclonal antibodies that specifically bind XOBESIN polypeptide fragment comprising the extracellular domain of mature XOBESIN polypeptide. Particularly preferred soluble fragment of XOBESIN comprises amino acids 30-197, 30-199, 30-207, 30-212, 30-224, 30-231, 30-245 or 30-262 of SEQ ID NO:2, where it is understood that amino acid 30 is predicted to be the N-terminal amino acid of the mature XOBESIN polypeptide absent the putative signal peptide.

EXAMPLES

The following Examples are provided for illustrative purposes and not as a means of limitation. One of ordinary skill in the art would be able to design equivalent assays and methods based on the disclosure herein all of which form part of the instant invention.

Example 1

Use of Biacore Technology to Detect Specific Binding of a Test Compound to Polypeptide Fragment Comprising XOBESIN Extracellular Domain Biacore utilizes a biosensor technology for monitoring interactions between two or more molecules in real time, without the use of labels. The molecular classes than can be studied are diverse, ranging from proteins, peptides, nucleic acids, carbohydrates, and lipids to low molecular weight substances and pharmaceuticals.

The detection principle is based on the optical phenomena of surface plasmon resonance, which detects changes in refractive index close to a biosensor surface. In a typical experiment one of the interacting molecules is immobilized or captured (here, polypeptide fragment comprising XOBESIN extracellular domain) to a flexible dextran layer close to the sensor surface. The interacting partner (here, test compound) is flowed across that surface. If an interaction occurs between the two molecules, there is a resulting increase in signal due to the increase in mass at the chip surface.

Soluble polypeptide fragment comprising XOBESIN extracellular domain is attached to the sensor surface via amine coupling chemistry. The dextran is activated using N-hydroxysuccinimide and N-ethyl-N'-(3-dimethylaminopropyl)-carbodiimide hydrochloride for 7 minutes. Said XOBESIN polypeptide fragment is diluted in 10 mM Na Acetate pH 5.0 at a concentration of 10 µg/ml and injected over the activated surface for 7 minutes. The surface is then blocked for 7 minutes using ethanolamine to remove any remaining esters. A blank flow cell absent said XOBESIN polypeptide fragment is set up in parallel and used as a control surface. The running buffer is HBS-EP (0.01M HEPES pH 7.4, 0.15M NaCl, 3 mM EDTA, 0.005% Surfactant P20) and the instrument temperature is 25° C.

The test compound is filtered through an Ultrafree-0.5 Centrifugal Filter Device and resuspended in HBS-EP running buffer. The test compound is then diluted 1:10 in HBS-EP and injected over the said XOBESIN polypeptide fragment surface and the blank control surface for 1 minute at a flow rate of 50 µl/min. The sensorgrams from the receptor surface and the control surface are aligned and overlayed.

To obtain the specific binding, the control surface was subtracted from the active surface comprised of said XOBESIN polypeptide fragment.

Example 2

Effect of LIGAND on Muscle Cell Fatty Acid Oxidation

C2C12 cells are differentiated in the presence or absence of 2 µg/mL LIGAND for 4 days. On day 4, oleate oxidation rates are determined by measuring conversion of 1-$^{14}$C-oleate (0.2 mM to $^{14}CO_2$ for 90 min. This experiment can be used to screen for active polypeptides and peptides as well as AGONISTS and ANTAGONISTS or activators and inhibitors of LIGAND receptor.

The effect of LIGAND on the rate of oleate oxidation can be compared in differentiated C2C12 cells (murine skeletal muscle cells; ATCC, Manassas, Va. CRL-1772) and in a hepatocyte cell line (Hepa1-6; ATCC, Manassas, Va. CRL-1830). Cultured cells are maintained according to manufacturer's instructions. The oleate oxidation assay is performed as previously described (Muoio et al (1999) Biochem J 338;783-791). Briefly, nearly confluent myocytes are kept in low serum differentiation media (MEM, 2.5% Horse serum) for 4 days, at which time formation of myotubes became maximal. Hepatocytes are kept in the same DMEM medium supplemented with 10% FCS for 2 days. One hour prior to the experiment the media is removed and 1 mL of preincubation media (MEM, 2.5% Horse serum, 3 mM glucose, 4 mM Glutamine, 25 mM Hepes, 1% FFA free BSA, 0.25 mM Oleate, 5 µg/mL gentamycin) is added. At the start of the oxidation experiment $^{14}$C-Oleic acid (1 µCi/mL, American Radiolabelled Chemical Inc., St. Louis, Mo.) is added and cells are incubated for 90 min at 37° C. in the absence/presence of 2.5 µm LIGAND. After the incubation period 0.75 mL of the media is removed and assayed for $^{14}$C-oxidation products as described below for the muscle FFA oxidation experiment.

Example 3

Effect of LIGAND on In Vitro Glucose Uptake by Muscle Cells

L6 Muscle cells are obtained from the European Culture Collection (Porton Down) and are used at passages 7-11. Cells are maintained in standard tissue culture medium DMEM, and glucose uptake is assessed using [$^3$H]-2-deoxyglucose (2DG) with or without LIGAND in the presence or absence of insulin ($10^{-8}$ M) as has been previously described (Walker, P. S. et al. (1990) Glucose transport activity in L6 muscle cells is regulated by the coordinate control of subcellular glucose transporter distribution, biosynthesis, and mRNA transcription. JBC 265(3):1516-1523; and Kilp, A. et al. (1992) Stimulation of hexose transport by metformin in L6 muscle cells in culture. Endocrinology 130(5):2535-2544, which disclosures are hereby incorporated by reference in their entireties). Uptake of 2DG is expressed as the percentage change compared with control (no added insulin or LIGAND). Values are presented as mean±SEM of sets of 4 wells per experiment. Differences between sets of wells are evaluated by Student's t test, probability values $p<0.05$ are considered to be significant.

Example 4

Effect of LIGAND on Mice Fed a High-Fat Diet

Experiments are performed using approximately 6 week old C57B1/6 mice (8 per group). All mice are housed individually. The mice are maintained on a high fat diet throughout each experiment. The high fat diet (cafeteria diet; D12331 from Research Diets, Inc.) has the following composition: protein kcal % 16, sucrose kcal % 26, and fat kcal % 58. The fat is primarily composed of coconut oil, hydrogenated.

After the mice are fed a high fat diet for 6 days, microosmotic pumps are inserted using isoflurane anesthesia, and are used to provide LIGAND, saline, and an irrelevant peptide to the mice subcutaneously (s.c.) for 18 days. LIGAND is provided at doses of 100, 50, 25, and 2.5 µg/day and the irrelevant peptide is provided at 10 µg/day. Body weight is measured on the first, third and fifth day of the high fat diet, and then daily after the start of treatment. Final blood samples are taken by cardiac puncture and are used to determine triglyceride (TG), total cholesterol (TC), glucose, leptin, and insulin levels. The amount of food consumed per day is also determined for each group.

Example 5

Effect of LIGAND on Plasma Free Fatty Acid in C57 BL/6 Mice

The effect of LIGAND on postprandial lipemia (PPL) in normal C57BL6/J mice is tested.

The mice used in this experiment are fasted for 2 hours prior to the experiment after which a baseline blood sample is taken. All blood samples are taken from the tail using EDTA coated capillary tubes (50 µL each time point). At time 0 (8:30 AM), a standard high fat meal (6 g butter, 6 g sunflower oil, 10 g nonfat dry milk, 10 g sucrose, 12 mL distilled water prepared fresh following Nb#6, JF, pg. 1) is given by gavage (vol.=1% of body weight) to all animals.

Immediately following the high fat meal, 25 µg a LIGAND is injected i.p. in 100 µL saline. The same dose (25 µg/mL in 100 µL) is again injected at 45 min and at 1 hr 45 min. Control animals are injected with saline (3×100 µL). Untreated and treated animals are handled in an alternating mode.

Blood samples are taken in hourly intervals, and are immediately put on ice. Plasma is prepared by centrifugation following each time point. Plasma is kept at –20° C. and free fatty acids (FFA), triglycerides (TG) and glucose are determined within 24 hours using standard test kits (Sigma and Wako). Due to the limited amount of plasma available, glucose is determined in duplicate using pooled samples. For each time point, equal volumes of plasma from all 8 animals per treatment group are pooled.

Example 6

Effect of LIGAND on Plasma FFA, TG and Glucose in C57 BL/6 Mice

Briefly, 14 mice re fasted for 2 hours prior to the experiment after which a baseline blood sample is taken. All blood samples are taken from the tail using EDTA coated capillary tubes (50 µL each time point). At time 0 (9:00 AM), a standard high fat meal (see Example 6) is given by gavage (vol.=1% of body weight) to all animals. Immediately following the high fat meal, 4 mice are injected 25 µg of LIGAND i.p. in 100 µL saline. The same dose (25 µg in 100 µL) is again injected at 45 min and at 1 hr 45 min. A second treatment group receives 3 times 50 µg LIGAND at the same intervals. Control animals are injected with saline (3×100 µL). Untreated and treated animals are handled in an alternating mode.

Blood samples are immediately put on ice. Plasma is prepared by centrifugation following each time point. Plasma is kept at –20° C. and free fatty acids (FFA), triglycerides (TG) and glucose are determined within 24 hours using standard test kits (Sigma and Wako).

Example 7

Effect of LIGAND on FFA Following Epinephrine Injection

In mice, plasma free fatty acids increase after intragastric administration of a high at/sucrose test meal. These free fatty acids are mostly produced by the activity of lipolytic enzymes i.e. lipoprotein lipase (LPL) and hepatic lipase (HL). In this species, these enzymes are found in significant amounts both bound to endothelium and freely circulating in plasma. Another source of plasma free fatty acids is hormone sensitive lipase (HSL) that releases free fatty acids from adipose issue after β-adrenergic stimulation. To test whether LIGAND also regulates the metabolism of free fatty acid released by HSL, mice are injected with epinephrine.

Two groups of mice are given epinephrine (5 µg) by intraperitoneal injection. A treated group is injected with a LIGAND (25 µg) one hour before and again together with epinephrine, while control animals receive saline. Plasma is isolated and free fatty acids and glucose are measured.

Example 8

Effect of LIGAND on FFA following Intralipid Injection

Two groups of mice are intravenously (tail vein) injected with 30 µL bolus of Intralipid-20% (Clintec) to generate a sudden rise in plasma FFAs, thus by-passing intestinal absorption. (Intralipid is an intravenous fat emulsion used in nutritional therapy). A treated group (LIGAND-treated) is injected with LIGAND (25 µg) at 30 and 60 minutes before intralipid is given, while control animals receive saline. Plasma is isolated and FFAs are measured as described previously. The effect of LIGAND on the decay in plasma FFAs following the peak induced by Intralipid injection is then monitored.

Example 9

Effect of LIGAND on Weight Gain and Weight Loss of Mice and on Maintenance of Weight Loss in Mice In the first experiment, 10-week-old male C57BL/6J mice are put on a very high fat/sucrose purified diet for 19 days to promote weight gain; the average body weight at this time is 30 g. The mice are then surgically implanted with an osmotic pump (Alzet, Newark, Del.) delivering either 2.5 µg/day of LIGAND or physiological saline. The mice are continued on the high fat diet and their body weight was recorded over the following 10-day period.

Weight gain by mice treated with saline in contradistinction to weight loss by mice treated with LIGAND is taken as evidence that in this inbred strain of normal mice, a continuous infusion of a daily low dose of LIGAND can prevent weight gain caused by high fat/sucrose feeding, in a sustainable way.

Data are expressed throughout as mean±SEM; a p-value<0.05 is considered statistically significant. Statistical analysis is typically done using either the unpaired Student's t test or the paired Student's t test.

Maintenance of Weight Loss in Mice

In order to demonstrate the ability of LIGAND to maintain weight loss, normal mice are put on a reduced calorie diet to promote weight loss. The reduced calorie diet is continued until the mice lose 10% of their initial weight. A second group of mice are continued on the reduced calorie diet until the mice lose 20% of their initial weight. The mice are then surgically implanted with an osmotic pump (Alzet, Newark, Del.) delivering either 2.5 µg/day of LIGAND or physiological saline. The mice are returned to a normal diet and their body weights are recorded over a 10-day period. After 10 days, the outcome wherein mice treated with LIGAND have a lower weight than mice treated with saline is taken to provide evidence that treatment with LIGAND promotes the maintenance of weight loss.

Example 10

Assessment of Homotrimer Formation by gAPM1, gC2P, gZADJ-2 or gZADJ-7 Polypeptide Fragment.

Homotrimer formation by gAPM1, gC2P, gZADJ-2 or gZADJ-7 polypeptide fragment is assessed using sedimentation equilibrium in analytical centrifuges, a method that determines molecular weight accurately and independently of other physical factors such as shape.

Candidate gAPM1, gC2P, gZADJ-2 or gZADJ-7 polypeptide fragment homotrimer is purified, for example using a protocol comprising a method of gel filtration such as 16/60 superdex 200 gel filtration column (Amersham). Said purified candidate gAPM1, gC2P, gZADJ-2 or gZADJ-7 polypeptide fragment homotrimer protein concentration is made 3 µM in 5.7 mM phosphate (pH 7.5), 137 mM NaCl, 2.7 mM KCl. Samples are centrifuged at 8,000 rpm for 18 hours at 10° C. in a Beckman XL-A analytical ultracentrifuge before absorbance is recorded. The data are fit globally, using MacNonlin PPC [Johnson M L et al., Biophys J (1981) 36:575-8; Schuster T M et al., Curr Opin Struct Biol (1996) 6:650-8; Hensley P, Structure (1996) 4:367-73; the disclosures of which are incorporated herein by reference in their entirety] to the following equation that describes the sedimentation of a homogeneous species: Abs=B+A'exp[H×M $(x^2-x_0^2)$] where Abs=absorbance at radius x, A'=absorbance at reference radius $x_0$, $H=(1-v\rho)\omega^2/2RT$, R=gas constant, T=temperature in Kelvin, v=partial specific volume=0.71896131 mL/g, ρ=density of solvent=1.0061 g/ml, ω=angular velocity in radians/s, M=apparent molecular weight, and B=solvent absorbance (blank).

TABLE 1

Amino Acid Residues Comprising the Structural Domains of XOBESIN SEQ ID NO: 2 Description

| SIGNAL PEPTIDE | EC DOMAIN | TRANSMEMBRANE DOMAIN | IC DOMAIN |
|---|---|---|---|
| 1-29 | 30-275 | 276-298 | 299 |

EC, extracellular domain; IC, intracellular domain

TABLE 2

APM1, C2P, ZADJ-2 and ZADJ-7

>APM1 polypeptide sequence:

(SEQ ID NO: 3)
MLLLGAVLLLLALPGHDQETTTQGPGVLLPLPKGACTGWMAGIPGHPGHN

GAPGRDGRDGTPGEKGEKGDPGLIGPKGDIGETGVPGAEGPRGFPGIQGR

KGEPGEGAYVYR<u>SAFSVGLETYVTIPNMPIRFTKIFYNQQNHYDGSTGKF</u>

<u>HCNIPGLYYFAYHITVYMKDVKVSLFKKDKAMLFTYDQYQENNVDQASGS</u>

<u>VLLHLEVGDQVWLQVYGEGERNGLYADNDNDSTFTGFLLYHDTN</u> (244)

>C2P polypeptide sequence:

(SEQ ID NO: 4)
MRIWWLLLAIEICTGNINSQDTCRQGHPGIPGNPGHNGLPGRDGRDGAKG

DKGDAGEPGRPGSPGKDGTSGEKGERGADGKVEAKGIKGDQGSRGSPGKH

GPKGLAGPMGEKGLRGETGPQGQKGNKGDVGPTGPEGPRGNIGPLGPTGL

PGPMGPIGKPGPKGEAGPTGPQGEPGVRGIRGWKGDRGEKGKIGETLVLP

K<u>SAFTVGLTVLSKFPSSDMPIKFDKILYNEFNHYDTAAGKFTCHIAGVYY</u>

<u>FTYHITVFSRNVQVSLVKNGVKILHTKDAYMSSEDQASGGIVLQLKLGDE</u>

<u>VWLQVTGGERFNGLFADEDDDTTFTGFLLFSSP</u> (333)

>ZADJ-2 polypeptide sequence:

(SEQ ID NO: 5)
MIPWVLLACALPCAADPLLGAFARRDFRKGSPQLVCSLPGPQGPPGPPGA

PGPSGMMGRMGFPGKDGQDGHDGDRGDSGEEGPPGRTGNRGKPGPKGKAG

AIGRAGPRGPKGVNGTPGKHGTPGKKGPKGKKGEPGLPGPCSCGSGHTK<u>S</u>

<u>AFSVAVTKSYPRERLPIKFDKILMNEGGHYNASSGKFVCGVPGIYYFTYD</u>

<u>ITLANKHLAIGLVHNGQYRIRTFDANTGNHDVASGSTILALKQGDEVWLQ</u>

<u>IFYSEQNGLFYDPYWTDSLFTGFLIYADQDDPNEV</u> (285)

TABLE 2-continued

APM1, C2P, ZADJ-2 and ZADJ-7

>ZADJ-7 polypeptide sequence:

(SEQ ID NO: 6)
MGKEDTQETRTEPKMFVLLYVTSFAICASGQPRGNQLKGENYSPRYICSI

PGLPGPPGPPGANGSPGPHGRIGLPGRDGRDGRKGEKGEKGTAGLRGKTG

PLGLAGEKGDQGETGKKGPIGPEGEKGEVGPIGPPGPKGDRGEQGDPGLP

GVCRCGSIVLK<u>SAFSVGITTSYPEERLPIIFNKVLFNEGEHYNPATGKFI</u>

<u>CAFPGIYYFSYDITLANKHLAIGLVHNGQYRIKTFDANTGNHDVASGSTV</u>

<u>IYLQPEDEVWLEIFFTDQNGLFSDPGWADSLFSGFLLYVDTDYLDSISED</u>

<u>DEL</u> (303)

---

What is claimed is:

1. A method of screening of a candidate agonist for interaction with a polypeptide comprising amino acids 30 to 275 of SEQ ID NO: 2, said method comprising the following steps:

a) providing a polypeptide comprising amino acids 30 to 275 of SEQ ID NO: 2;

b) obtaining a composition comprising a candidate agonist of the polypeptide comprising amino acids 30 to 275 of SEQ ID NO: 2;

c) bringing into contact said polypeptide with said candidate agonist;

d) detecting the complexes formed between said polypeptide and said candidate agonist;

wherein said detecting comprises:

(a) assaying for the stimulation of muscle lipid or free fatty acid oxidation in vitro;

(b) assaying, in vitro, for an increase in leptin uptake in a liver cell line.

2. The method according to claim 1, wherein said detecting step comprises assaying for the stimulation of muscle lipid or free fatty acid oxidation in vitro.

3. The method according to claim 1, wherein said candidate agonist is a composition consisting essentially of self-assembling homotrimers comprising fragments of SEQ ID NO: 3 (gAPM 1), SEQ ID NO: 4 (gC2P), SEQ ID NO: 5 (gZADJ2) or SEQ ID NO: 6 (gZADJ-7), said fragments comprising a NGLXXD motif and a Clq homology domain comprising amino acids 113 to 244 of SEQ ID NO: 3 (gApm 1), amino acids 202 to 333 of SEQ ID NO: 4 (gC2P), amino acids 150 to 285 of SEQ ID NO: 5 (gZADJ2), or amino acids 162 to 303 of SEQ ID NO: 6 (gZADJ-7).

4. The method according to claim 1, wherein said candidate agonist is a composition consisting essentially of self-assembling homotrimers comprising SEQ ID NO: 3 (gAPM1), SEQ ID NO: 4 (gC2P), SEQ ID NO: 5 (gZADJ2) or SEQ ID NO: 6 (gZADJ-7).

* * * * *

SEQUENCE LISTING

<160> NUMBER OF SEQ ID NOS: 6

<210> SEQ ID NO 1
<211> LENGTH: 1365
<212> TYPE: DNA
<213> ORGANISM: Homo sapiens
<220> FEATURE:
<221> NAME/KEY: CDS
<222> LOCATION: (30)...(929)

<400> SEQUENCE: 1

```
gaattcggca cgagggagtt tgaccagag atg caa ggg gtg aag gag cgc ttc         53
                                 Met Gln Gly Val Lys Glu Arg Phe
                                  1               5 cta ccg tta ggg aac tct ggg gac aga gcg ccc cgg ccg cct gat ggc        101
Leu Pro Leu Gly Asn Ser Gly Asp Arg Ala Pro Arg Pro Pro Asp Gly
         10                  15                  20 cga ggc agg gtg cga ccc agg acc cag gac ggc gtc ggg aac cat acc        149
Arg Gly Arg Val Arg Pro Arg Thr Gln Asp Gly Val Gly Asn His Thr
 25                  30                  35                  40 atg gcc cgg atc ccc aag acc cta aag ttc gtc gtc gtc atc gtc gcg        197
Met Ala Arg Ile Pro Lys Thr Leu Lys Phe Val Val Val Ile Val Ala
                 45                  50                  55 gtc ctg ctg cca gtc cta gct tac tct gcc acc act gcc cgg cag gag        245
Val Leu Leu Pro Val Leu Ala Tyr Ser Ala Thr Thr Ala Arg Gln Glu
             60                  65                  70 gaa gtt ccc cag cag aca gtg gcc cca cag caa cag agg cac agc ttc        293
Glu Val Pro Gln Gln Thr Val Ala Pro Gln Gln Gln Arg His Ser Phe
         75                  80                  85 aag ggg gag gag tgt cca gca gga tct cat aga tca gaa cat act gga        341
Lys Gly Glu Glu Cys Pro Ala Gly Ser His Arg Ser Glu His Thr Gly
 90                  95                 100 gcc tgt aac ccg tgc aca gag ggt gtg gat tac acc aac gct tcc aac        389
Ala Cys Asn Pro Cys Thr Glu Gly Val Asp Tyr Thr Asn Ala Ser Asn
105                 110                 115                 120 aat gaa cct tct tgc ttc cca tgt aca gtt tgt aaa tca gat caa aaa        437
Asn Glu Pro Ser Cys Phe Pro Cys Thr Val Cys Lys Ser Asp Gln Lys
                125                 130                 135 cat aaa agt tcc tgc acc atg acc aga gac aca gtg tgt cag tgt aaa        485
His Lys Ser Ser Cys Thr Met Thr Arg Asp Thr Val Cys Gln Cys Lys
            140                 145                 150
```

-continued

```
gaa ggc acc ttc cgg aat gaa aac tcc cca gag atg tgc cgg aag tgt       533
Glu Gly Thr Phe Arg Asn Glu Asn Ser Pro Glu Met Cys Arg Lys Cys
        155                 160                 165 agc agg tgc cct agt ggg gaa gtc caa gtc agt aat tgt acg tcc tgg       581
Ser Arg Cys Pro Ser Gly Glu Val Gln Val Ser Asn Cys Thr Ser Trp
    170                 175                 180 gat gat atc cag tgt gtt gaa gaa ttt ggt gcc aat gcc act gtg gaa       629
Asp Asp Ile Gln Cys Val Glu Glu Phe Gly Ala Asn Ala Thr Val Glu
185                 190                 195                 200 acc cca gct gct gaa gag aca atg aac acc agc ccg ggg act cct gcc       677
Thr Pro Ala Ala Glu Glu Thr Met Asn Thr Ser Pro Gly Thr Pro Ala
                205                 210                 215 cca gct gct gaa gag aca atg aac acc agc cca ggg act cct gcc cca       725
Pro Ala Ala Glu Glu Thr Met Asn Thr Ser Pro Gly Thr Pro Ala Pro
            220                 225                 230 gct gct gaa gag aca atg acc acc agc ccg ggg act cct gcc cca gct       773
Ala Ala Glu Glu Thr Met Thr Thr Ser Pro Gly Thr Pro Ala Pro Ala
        235                 240                 245 gct gaa gag aca atg acc acc agc ccg ggg act cct gcc cca gct gct       821
Ala Glu Glu Thr Met Thr Thr Ser Pro Gly Thr Pro Ala Pro Ala Ala
    250                 255                 260 gaa gag aca atg acc acc agc ccg ggg act cct gcc tct tct cat tac       869
Glu Glu Thr Met Thr Thr Ser Pro Gly Thr Pro Ala Ser Ser His Tyr
265                 270                 275                 280 ctc tca tgc acc atc gta ggg atc ata gtt cta att gtg ctt ctg att       917
Leu Ser Cys Thr Ile Val Gly Ile Ile Val Leu Ile Val Leu Leu Ile
                285                 290                 295 gtg ttt gtt tga aagacttcac tgtggaagaa attccttcct tacctgaaag           969
Val Phe Val * gttcaggtag cgctggctg agggcggggg gcgctggaca ctctctgccc tgcctccctc     1029
tgctgtgttc ccacagacag aaacgcctgc ccctgcccca agtcctggtg tctccagcct    1089
ggctctatct tcctccttgt gatcgtccca tccccacatc ccgtgcaccc cccaggaccc    1149
tggtctcatc agtccctctc ctggagctgg gggtccacac atctcccagc caagtccaag    1209
agggcagggc cagttcctcc catcttcagg cccagccagg caggggcag tcggctcctc     1269 aactgggtga caagggtgag gatgagaagt ggtcacggga tttattcagc cttggtcaga    1329
gcagaaaaaa aaaaaaaaaa aaaagatctt taatta                              1365
```

<210> SEQ ID NO 2
<211> LENGTH: 299
<212> TYPE: PRT
<213> ORGANISM: Homo sapiens
<220> FEATURE:
<221> NAME/KEY: VARIANT
<222> LOCATION: 159
<223> OTHER INFORMATION: Polymorphic amino acid Glu or Val
<220> FEATURE:
<221> NAME/KEY: VARIANT
<222> LOCATION: 207
<223> OTHER INFORMATION: Polymorphic amino acid Thr or Arg

<400> SEQUENCE: 2

```
Met Gln Gly Val Lys Glu Arg Phe Leu Pro Leu Gly Asn Ser Gly Asp
1               5                   10                  15

Arg Ala Pro Arg Pro Pro Asp Gly Arg Gly Arg Val Arg Pro Arg Thr
            20                  25                  30

Gln Asp Gly Val Gly Asn His Thr Met Ala Arg Ile Pro Lys Thr Leu
        35                  40                  45
```

```
Lys Phe Val Val Val Ile Val Ala Val Leu Leu Pro Val Leu Ala Tyr
         50                  55                  60

Ser Ala Thr Thr Ala Arg Gln Glu Val Pro Gln Gln Thr Val Ala
 65                  70                  75                  80

Pro Gln Gln Arg His Ser Phe Lys Gly Glu Glu Cys Pro Ala Gly
                 85                  90                  95

Ser His Arg Ser Glu His Thr Gly Ala Cys Asn Pro Cys Thr Glu Gly
                100                 105                 110

Val Asp Tyr Thr Asn Ala Ser Asn Asn Glu Pro Ser Cys Phe Pro Cys
            115                 120                 125

Thr Val Cys Lys Ser Asp Gln Lys His Lys Ser Ser Cys Thr Met Thr
130                 135                 140

Arg Asp Thr Val Cys Gln Cys Lys Glu Gly Thr Phe Arg Asn Glu Asn
145                 150                 155                 160

Ser Pro Glu Met Cys Arg Lys Cys Ser Arg Cys Pro Ser Gly Glu Val
                165                 170                 175

Gln Val Ser Asn Cys Thr Ser Trp Asp Asp Ile Gln Cys Val Glu Glu
            180                 185                 190

Phe Gly Ala Asn Ala Thr Val Glu Thr Pro Ala Ala Glu Glu Thr Met
        195                 200                 205

Asn Thr Ser Pro Gly Thr Pro Ala Pro Ala Ala Glu Glu Thr Met Asn
210                 215                 220

Thr Ser Pro Gly Thr Pro Ala Pro Ala Ala Glu Glu Thr Met Thr Thr
225                 230                 235                 240

Ser Pro Gly Thr Pro Ala Pro Ala Ala Glu Glu Thr Met Thr Thr Ser
                245                 250                 255

Pro Gly Thr Pro Ala Pro Ala Ala Glu Glu Thr Met Thr Thr Ser Pro
            260                 265                 270

Gly Thr Pro Ala Ser Ser His Tyr Leu Ser Cys Thr Ile Val Gly Ile
        275                 280                 285

Ile Val Leu Ile Val Leu Leu Ile Val Phe Val
290                 295

<210> SEQ ID NO 3
<211> LENGTH: 244
<212> TYPE: PRT
<213> ORGANISM: Homo sapiens

<400> SEQUENCE: 3

Met Leu Leu Leu Gly Ala Val Leu Leu Leu Ala Leu Pro Gly His
 1               5                  10                  15

Asp Gln Glu Thr Thr Thr Gln Gly Pro Gly Val Leu Leu Pro Leu Pro
                 20                  25                  30

Lys Gly Ala Cys Thr Gly Trp Met Ala Gly Ile Pro Gly His Pro Gly
             35                  40                  45

His Asn Gly Ala Pro Gly Arg Asp Gly Arg Asp Gly Thr Pro Gly Glu
         50                  55                  60

Lys Gly Glu Lys Gly Asp Pro Gly Leu Ile Gly Pro Lys Gly Asp Ile
 65                  70                  75                  80

Gly Glu Thr Gly Val Pro Gly Ala Glu Gly Pro Arg Gly Phe Pro Gly
                 85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125
```

```
Pro Ile Arg Phe Thr Lys Ile Phe Tyr Asn Gln Gln Asn His Tyr Asp
    130                 135                 140
Gly Ser Thr Gly Lys Phe His Cys Asn Ile Pro Gly Leu Tyr Tyr Phe
145                 150                 155                 160
Ala Tyr His Ile Thr Val Tyr Met Lys Asp Val Lys Val Ser Leu Phe
                165                 170                 175
Lys Lys Asp Lys Ala Met Leu Phe Thr Tyr Asp Gln Tyr Gln Glu Asn
            180                 185                 190
Asn Val Asp Gln Ala Ser Gly Ser Val Leu Leu His Leu Glu Val Gly
        195                 200                 205
Asp Gln Val Trp Leu Gln Val Tyr Gly Glu Gly Glu Arg Asn Gly Leu
    210                 215                 220
Tyr Ala Asp Asn Asp Asn Asp Ser Thr Phe Thr Gly Phe Leu Leu Tyr
225                 230                 235                 240
His Asp Thr Asn
```

<210> SEQ ID NO 4
<211> LENGTH: 333
<212> TYPE: PRT
<213> ORGANISM: Homo sapiens

<400> SEQUENCE: 4

```
Met Arg Ile Trp Trp Leu Leu Leu Ala Ile Glu Ile Cys Thr Gly Asn
1               5                   10                  15
Ile Asn Ser Gln Asp Thr Cys Arg Gln Gly His Pro Gly Ile Pro Gly
            20                  25                  30
Asn Pro Gly His Asn Gly Leu Pro Gly Arg Asp Gly Arg Asp Gly Ala
        35                  40                  45
Lys Gly Asp Lys Gly Asp Ala Gly Glu Pro Gly Arg Pro Gly Ser Pro
    50                  55                  60
Gly Lys Asp Gly Thr Ser Gly Glu Lys Gly Glu Arg Gly Ala Asp Gly
65                  70                  75                  80
Lys Val Glu Ala Lys Gly Ile Lys Gly Asp Gln Gly Ser Arg Gly Ser
                85                  90                  95
Pro Gly Lys His Gly Pro Lys Gly Leu Ala Gly Pro Met Gly Glu Lys
            100                 105                 110
Gly Leu Arg Gly Glu Thr Gly Pro Gln Gly Gln Lys Gly Asn Lys Gly
        115                 120                 125
Asp Val Gly Pro Thr Gly Pro Glu Gly Pro Arg Gly Asn Ile Gly Pro
    130                 135                 140
Leu Gly Pro Thr Gly Leu Pro Gly Pro Met Gly Pro Ile Gly Lys Pro
145                 150                 155                 160
Gly Pro Lys Gly Glu Ala Gly Pro Thr Gly Pro Gln Gly Glu Pro Gly
                165                 170                 175
Val Arg Gly Ile Arg Gly Trp Lys Gly Asp Arg Gly Glu Lys Gly Lys
            180                 185                 190
Ile Gly Glu Thr Leu Val Leu Pro Lys Ser Ala Phe Thr Val Gly Leu
        195                 200                 205
Thr Val Leu Ser Lys Phe Pro Ser Ser Asp Met Pro Ile Lys Phe Asp
    210                 215                 220
Lys Ile Leu Tyr Asn Glu Phe Asn His Tyr Asp Thr Ala Ala Gly Lys
225                 230                 235                 240
Phe Thr Cys His Ile Ala Gly Val Tyr Tyr Phe Thr Tyr His Ile Thr
                245                 250                 255
```

```
Val Phe Ser Arg Asn Val Gln Val Ser Leu Val Lys Asn Gly Val Lys
            260                 265                 270

Ile Leu His Thr Lys Asp Ala Tyr Met Ser Ser Glu Asp Gln Ala Ser
            275                 280                 285

Gly Gly Ile Val Leu Gln Leu Lys Leu Gly Asp Glu Val Trp Leu Gln
            290                 295                 300

Val Thr Gly Gly Glu Arg Phe Asn Gly Leu Phe Ala Asp Glu Asp Asp
305                 310                 315                 320

Asp Thr Thr Phe Thr Gly Phe Leu Leu Phe Ser Ser Pro
            325                 330

<210> SEQ ID NO 5
<211> LENGTH: 285
<212> TYPE: PRT
<213> ORGANISM: Homo sapiens

<400> SEQUENCE: 5

Met Ile Pro Trp Val Leu Leu Ala Cys Ala Leu Pro Cys Ala Ala Asp
1               5                   10                  15

Pro Leu Leu Gly Ala Phe Ala Arg Arg Asp Phe Arg Lys Gly Ser Pro
            20                  25                  30

Gln Leu Val Cys Ser Leu Pro Gly Pro Gln Gly Pro Pro Gly Pro Pro
        35                  40                  45

Gly Ala Pro Gly Pro Ser Gly Met Met Gly Arg Met Gly Phe Pro Gly
    50                  55                  60

Lys Asp Gly Gln Asp Gly His Asp Gly Asp Arg Gly Asp Ser Gly Glu
65                  70                  75                  80

Glu Gly Pro Pro Gly Arg Thr Gly Asn Arg Gly Lys Pro Gly Pro Lys
                85                  90                  95

Gly Lys Ala Gly Ala Ile Gly Arg Ala Gly Pro Arg Gly Pro Lys Gly
            100                 105                 110

Val Asn Gly Thr Pro Gly Lys His Gly Thr Pro Gly Lys Lys Gly Pro
        115                 120                 125

Lys Gly Lys Lys Gly Glu Pro Gly Leu Pro Gly Pro Cys Ser Cys Gly
130                 135                 140

Ser Gly His Thr Lys Ser Ala Phe Ser Val Ala Val Thr Lys Ser Tyr
145                 150                 155                 160

Pro Arg Glu Arg Leu Pro Ile Lys Phe Asp Lys Ile Leu Met Asn Glu
                165                 170                 175

Gly Gly His Tyr Asn Ala Ser Ser Gly Lys Phe Val Cys Gly Val Pro
            180                 185                 190

Gly Ile Tyr Tyr Phe Thr Tyr Asp Ile Thr Leu Ala Asn Lys His Leu
        195                 200                 205

Ala Ile Gly Leu Val His Asn Gly Gln Tyr Arg Ile Arg Thr Phe Asp
    210                 215                 220

Ala Asn Thr Gly Asn His Asp Val Ala Ser Gly Ser Thr Ile Leu Ala
225                 230                 235                 240

Leu Lys Gln Gly Asp Glu Val Trp Leu Gln Ile Phe Tyr Ser Glu Gln
                245                 250                 255

Asn Gly Leu Phe Tyr Asp Pro Tyr Trp Thr Asp Ser Leu Phe Thr Gly
            260                 265                 270

Phe Leu Ile Tyr Ala Asp Gln Asp Asp Pro Asn Glu Val
        275                 280                 285
```

-continued

```
<210> SEQ ID NO 6
<211> LENGTH: 303
<212> TYPE: PRT
<213> ORGANISM: Homo sapiens

<400> SEQUENCE: 6

Met Gly Lys Glu Asp Thr Gln Glu Thr Arg Thr Glu Pro Lys Met Phe
1               5                   10                  15

Val Leu Leu Tyr Val Thr Ser Phe Ala Ile Cys Ala Ser Gly Gln Pro
            20                  25                  30

Arg Gly Asn Gln Leu Lys Gly Glu Asn Tyr Ser Pro Arg Tyr Ile Cys
        35                  40                  45

Ser Ile Pro Gly Leu Pro Gly Pro Pro Gly Pro Pro Gly Ala Asn Gly
    50                  55                  60

Ser Pro Gly Pro His Gly Arg Ile Gly Leu Pro Gly Arg Asp Gly Arg
65                  70                  75                  80

Asp Gly Arg Lys Gly Glu Lys Gly Glu Lys Gly Thr Ala Gly Leu Arg
                85                  90                  95

Gly Lys Thr Gly Pro Leu Gly Leu Ala Gly Glu Lys Gly Asp Gln Gly
            100                 105                 110

Glu Thr Gly Lys Lys Gly Pro Ile Gly Pro Glu Gly Glu Lys Gly Glu
        115                 120                 125

Val Gly Pro Ile Gly Pro Pro Gly Pro Lys Gly Asp Arg Gly Glu Gln
    130                 135                 140

Gly Asp Pro Gly Leu Pro Gly Val Cys Arg Cys Gly Ser Ile Val Leu
145                 150                 155                 160

Lys Ser Ala Phe Ser Val Gly Ile Thr Thr Ser Tyr Pro Glu Glu Arg
                165                 170                 175

Leu Pro Ile Ile Phe Asn Lys Val Leu Phe Asn Glu Gly Glu His Tyr
            180                 185                 190

Asn Pro Ala Thr Gly Lys Phe Ile Cys Ala Phe Pro Gly Ile Tyr Tyr
        195                 200                 205

Phe Ser Tyr Asp Ile Thr Leu Ala Asn Lys His Leu Ala Ile Gly Leu
    210                 215                 220

Val His Asn Gly Gln Tyr Arg Ile Lys Thr Phe Asp Ala Asn Thr Gly
225                 230                 235                 240

Asn His Asp Val Ala Ser Gly Ser Thr Val Ile Tyr Leu Gln Pro Glu
                245                 250                 255

Asp Glu Val Trp Leu Glu Ile Phe Phe Thr Asp Gln Asn Gly Leu Phe
            260                 265                 270

Ser Asp Pro Gly Trp Ala Asp Ser Leu Phe Ser Gly Phe Leu Leu Tyr
        275                 280                 285

Val Asp Thr Asp Tyr Leu Asp Ser Ile Ser Glu Asp Glu Leu
    290                 295                 300
```